(12) United States Patent
Hall

(10) Patent No.: US 6,758,084 B2
(45) Date of Patent: Jul. 6, 2004

(54) METHOD AND APPARATUS FOR DETECTING A DRY/WET STATE OF A THERMISTOR BEAD

(75) Inventor: Robbie William Hall, Charlotte, VT (US)

(73) Assignee: Simmonds Precision Products, Inc., Charlotte, NC (US)

(*) Notice: Subject to any disclaimer, the term of this patent is extended or adjusted under 35 U.S.C. 154(b) by 0 days.

(21) Appl. No.: 10/279,668

(22) Filed: Oct. 24, 2002

(65) Prior Publication Data

US 2004/0080423 A1 Apr. 29, 2004

(51) Int. Cl.[7] ............................................. G01N 25/56
(52) U.S. Cl. .............................. 73/73; 73/77; 340/604; 324/664
(58) Field of Search ....................... 73/73, 77; 340/604; 324/664, 665

(56) References Cited

U.S. PATENT DOCUMENTS

| | | | | |
|---|---|---|---|---|
| 4,872,340 A | * | 10/1989 | de Yong | 73/335.02 |
| 4,901,061 A | * | 2/1990 | Twerdochlib | 340/604 |
| 5,534,708 A | * | 7/1996 | Ellinger et al. | 250/577 |
| 5,880,480 A | * | 3/1999 | Ellinger et al. | 250/577 |
| 6,208,254 B1 | * | 3/2001 | McQueen et al. | 340/603 |

* cited by examiner

*Primary Examiner*—Hezron Williams
*Assistant Examiner*—Rodney Frank
(74) *Attorney, Agent, or Firm*—David R. Percio; Calfee, Halter & Griswold, LLP

(57) ABSTRACT

A method of detecting a dry/wet state of a thermistor bead comprises the steps of: conducting current through the thermistor bead selectively between first and second current levels; measuring a difference in voltage across the thermistor bead in response to the first and second current levels; and detecting the dry/wet state of the thermistor bead based on the measured difference in voltage. In one embodiment, the first and second current levels conducted through the thermistor bead are both less than thirty milliamps. Apparatus for embodying this detection method is also disclosed.

20 Claims, 4 Drawing Sheets

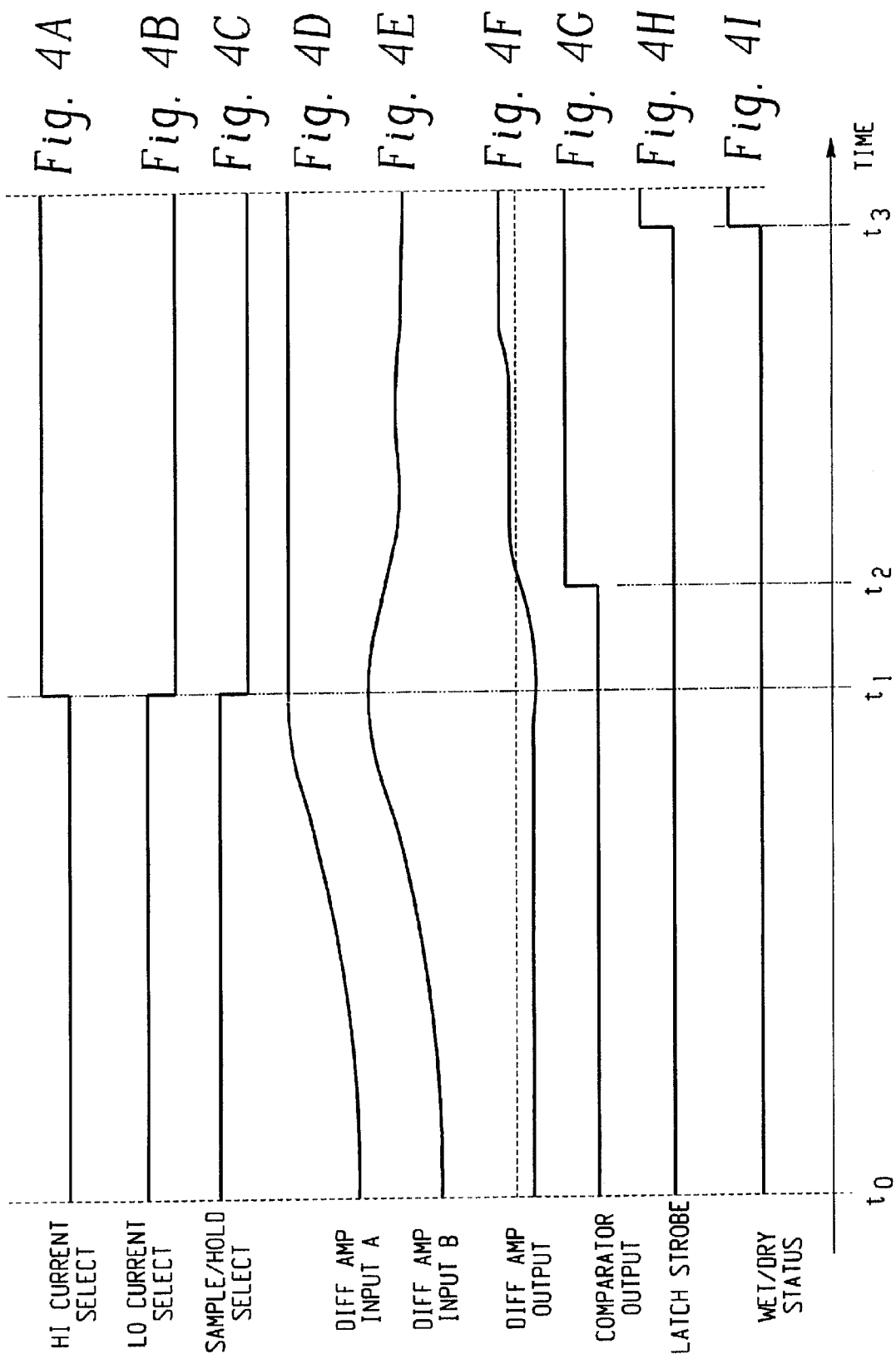

US 6,758,084 B2

METHOD AND APPARATUS FOR DETECTING A DRY/WET STATE OF A THERMISTOR BEAD

BACKGROUND OF THE INVENTION

The present invention is directed to the detection of dry/wet states of a thermistor bead, in general, and more particularly, to a method and apparatus for detecting a dry/wet state of a thermistor bead based on a difference in voltage across the thermistor bead in response to a difference in current conducted therethrough.

Sensing liquid level in a container, like fuel in an aircraft fuel tank, for example, has been performed using resistive bead type thermistors which have an inverse temperature coefficient. When current is conducted through a thermistor bead in air, i.e. a dry state, the bead increases in temperature and exhibits a low resistance to the current. In contrast, when the thermistor bead is submersed in a liquid, like jet fuel, for example, the bead is cooled and its resistance to current conducted therethrough is increased. Current vs. Voltage (I/V) characteristics of a typical thermistor bead at various temperatures is shown in the graph of FIG. 1. It is readily observable from the graph of FIG. 1 that the voltage across the thermistor becomes a viable measurement for detecting a wet vs. dry (wet/dry) state of the thermistor bead as the current conducted therethrough becomes greater than 45 milliamps. For example, by passing a constant current through a thermistor bead and lowering the bead from the top of the container, it may be determined at what level in the container the thermistor bead becomes submersed into the liquid by detecting the wet/dry state thereof based on the voltage across the thermistor bead.

Known interface circuitry which uses the above described method of detecting the dry/wet state of a thermistor bead is shown in the block diagram schematic of FIG. 2. Referring to FIG. 2, a thermistor bead 10 is coupled between a constant current source 12 and a common or ground return. The constant current source 12 is powered by a power supply and is operative to conduct current through the thermistor bead 10. The voltage across the thermistor bead 10 is sensed by one input of a comparator circuit 16 which is also powered by the supply 14 and common return. A reference voltage is generated by a circuit 18 which is powered by the supply 14. The comparator circuit 16 compares the reference voltage which is coupled to another input thereof with the thermistor bead voltage. When the thermistor bead voltage exceeds the reference voltage, a wet bead state is effected at the output of the comparator 16 and when the thermistor bead voltage is less than the reference voltage, a dry bead state is effected at the output of the comparator 16.

As noted above, to insure proper performance of the thermistor bead and detection circuitry using the above described method, the bead 10 should be biased with a constant current equal to or greater than 45 milliamps where voltage levels across the bead are dry/wet distinct for all practical temperature environments ( see the graphs of FIG. 1, for example). For level sensing of combustible liquids in a container with a thermistor bead, the bias current level of 45 milliamps may not be considered safe, and thus unacceptable. For example, the FAA has deemed this bias current level unacceptable in terms of the maximum allowable current that may enter an aircraft fuel tank. Only currents less than 30 milliamps with justification have been deemed acceptable for aircraft fuel tanks. Accordingly, a thermistor bead may not be an acceptable level measurement sensor for combustible liquids in all cases using interface circuitry implementing the above described traditional method.

SUMMARY OF THE INVENTION

In accordance with one aspect of the present invention, a method of detecting a dry/wet state of a thermistor bead comprises the steps of: conducting current through the thermistor bead selectively between first and second current levels; measuring a difference in voltage across the thermistor bead in response to the first and second current levels; and detecting the dry/wet state of the thermistor bead based on the measured difference in voltage. In one embodiment, the first and second current levels conducted through the thermistor bead are both less than thirty milliamps.

In accordance with another aspect of the present invention, apparatus for detecting a dry/wet state of a thermistor bead comprises: a first circuit coupled to the thermistor bead for conducting current through the thermistor bead selectively between first and second current levels; a second circuit coupled to the thermistor bead for measuring a difference in voltage across the thermistor bead in response to the first and second current levels; and a third circuit coupled to the second circuit for detecting the dry/wet state of the thermistor bead based on the measured difference in voltage.

BRIEF DESCRIPTION OF THE DRAWINGS

FIGS. 4A–4I are time graphs suitable for use in describing the operation of the embodiment of FIG. 3.

DETAILED DESCRIPTION OF THE INVENTION

Figure 1:
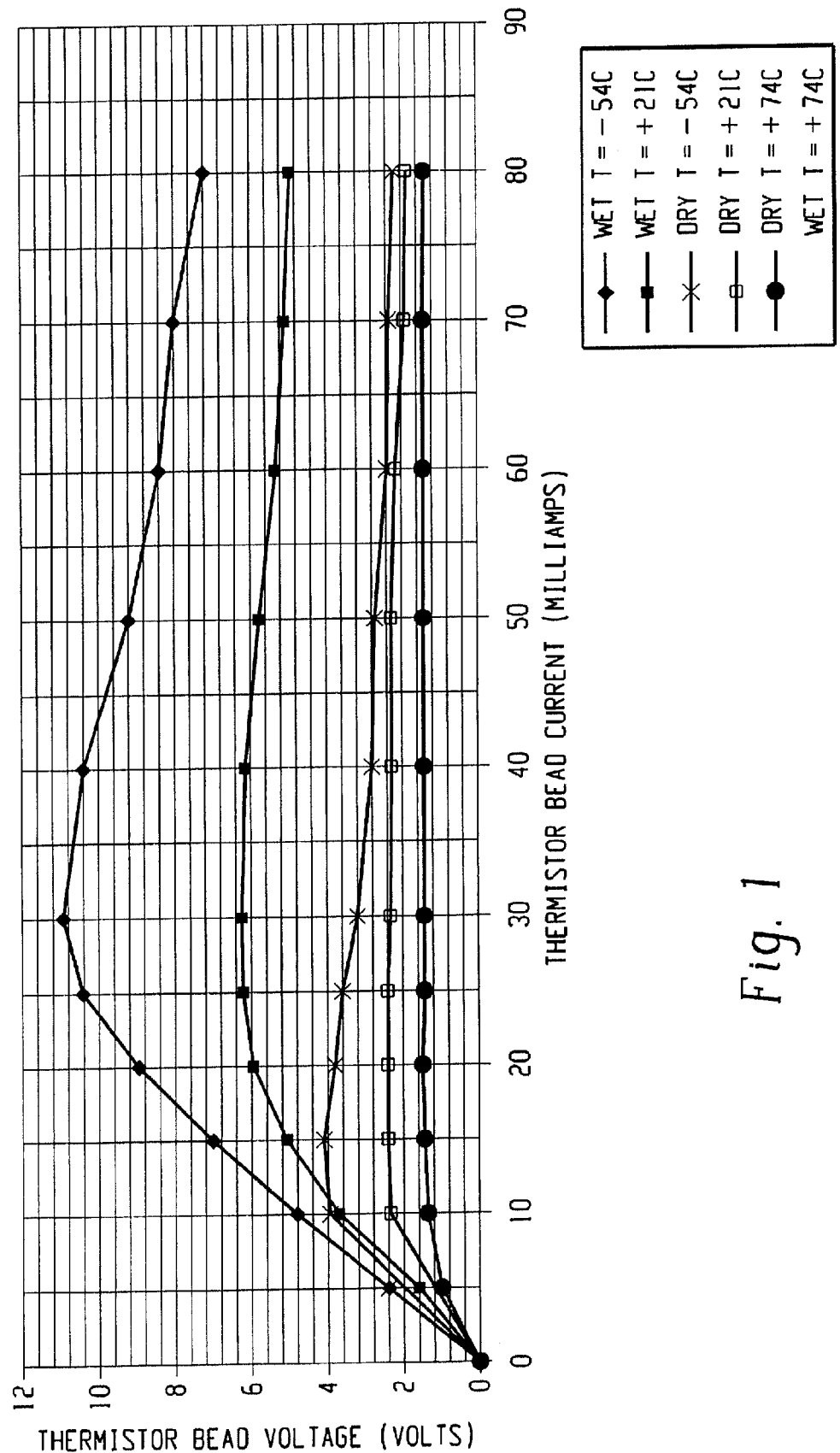
FIG. 1 is a graph depicting dry and wet current vs. voltage characteristics of a typical thermistor bead at various temperatures.
Figure 2:
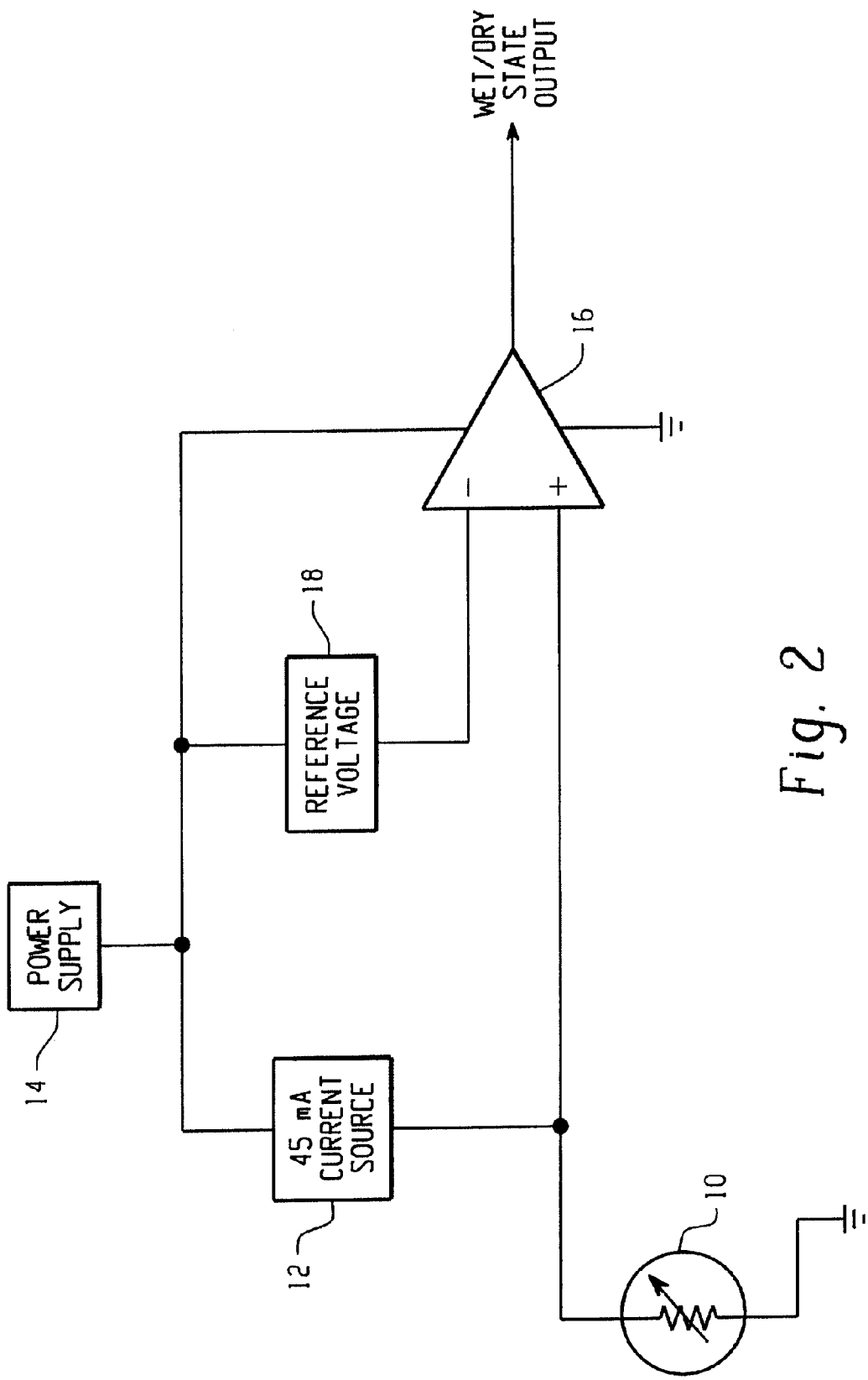
FIG. 2 is a block diagram circuit schematic of interface circuitry for detecting the dry/wet state of a thermistor bead based on a known method.

The method and apparatus of the present invention detects the dry/wet state of a thermistor bead for liquid level measurement, but is capable of performing the dry/wet state detection thereof using bias currents substantially less than forty-five milliamps. This method and apparatus may even operate with bias currents less than thirty milliamps for thermistor bead application to measurement of fuel level in an aircraft fuel tank which is considered within the FAA acceptable current levels. As shown in FIG. 1, for all temperature conditions, the current vs. voltage (I/V) characteristics of a thermistor bead at bias currents of less than thirty milliamps (30 ma), and more particularly between fifteen milliamps (15 ma) and twenty-five milliamps (25 ma), for example, the I/V slope characteristics of a dry bead are either less than the I/V slope characteristics of a wet bead or are negative. Thus, the dry/wet state of the thermistor bead for fuel level application in an aircraft fuel tank may be detected based on a voltage slope determination in response to two different bias currents that are both less than thirty milliamps, and thus acceptable from a safety perspective.

Figure 3:
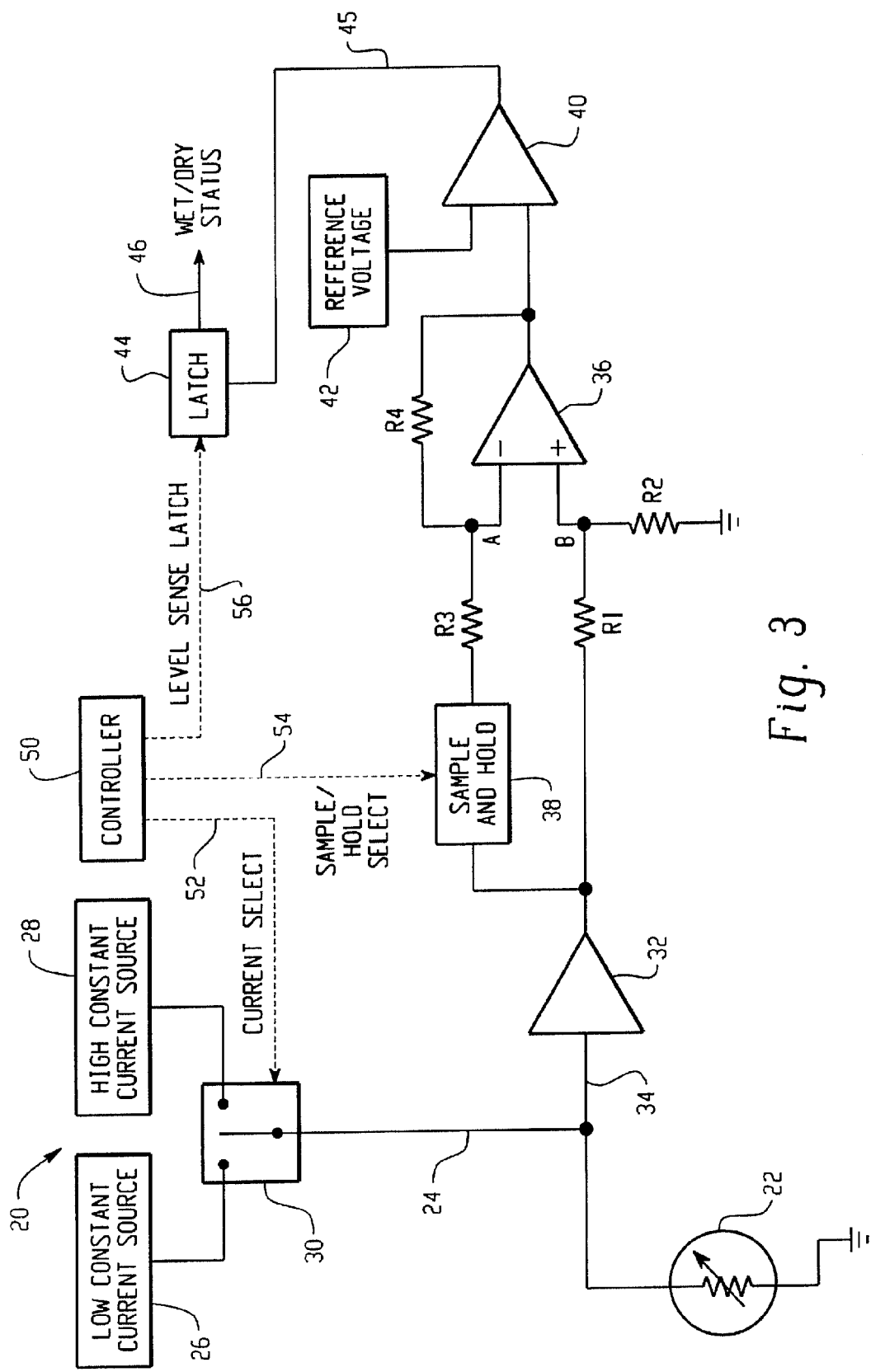
FIG. 3 is a block diagram circuit schematic of apparatus for detecting the dry/wet state of a thermistor bead suitable for embodying the broad principles of the present invention.

A block diagram schematic of apparatus for detecting the dry/wet state of a thermistor bead suitable for embodying the principles of the present invention is shown in FIG. 3. Referring to FIG. 3, a constant current source 20 is coupled to a thermistor bead 22 over a signal line 24. The source 20 is operative to conduct current through the thermistor bead selectively between a first or low current level, like on the order of fifteen milliamps, for example, and a second or high current level, like on the order of twenty-five milliamps, for example. In the present embodiment, the constant current source 20 includes a first or low constant current source 26 for generating current at the first current level, a second constant current source 28 for generating current at the second current level, and a switch 30 for coupling selectively the first and second constant current sources to the thermistor bead 22 over signal 24 for conducting the selected current through the thermistor bead 22 to a common potential. While two constant current sources are used in the present embodiment for the constant current source 20, it is understood that a single constant current source which is selectively controlled to generate either the first current level or second current level may be used just as well without deviating from the broad principles of the present invention.

The voltage developed across the thermistor bead 22 in response to the selected current level may be amplified and buffered by an amplifier circuit 32 which is coupled to the thermistor bead 22 by a signal line 34, for example. An output of the amplifier circuit 32 is coupled to a noninverting (+) or B input of a differential amplifier circuit 36 via a resistor divider network comprising resistors R1 and R2 coupled in series between amplifier 32 and the common potential. Also coupled to the output of amplifier 32 is a sample-and-hold circuit 38, the output of which being coupled to an inverting (−) or A input of the differential amplifier 36 through a resistor R3. Another resistor R4 is coupled between the output and A input of the amplifier 36. The ratio of resistor values R4 to R3 sets the closed loop gain of the differential amplifier 36.

Still referring to FIG. 3, the output of amplifier 36 is coupled to one input of a comparator circuit 40. A reference voltage generator circuit generates a reference voltage signal which is coupled to another input of comparator circuit 40. An output of comparator 40 may be coupled over a signal line 45 to a latch circuit 44 which provides a signal indicative of the dry/wet state of the thermistor bead 22 over an output signal line 46. In the present embodiment, a controller circuit 50 is coupled to the constant current source 20 via switch 30, the sample-and-hold circuit 38, and the latch circuit 44 over signal lines 52, 54 and 56, respectively, for the time sequence control of the operations thereof as will become more evident from the description provided herein below in connection with the time graphs of FIGS. 4A–4I.

Referring to FIG. 3 and the time graphs pf FIGS. 4A–4I, at time to, controller 50 is operative to control the constant current circuit 20 to conduct current at the first or low current level through the thermistor bead 22 for a period of time, like until time $t_1$, for example. This is accomplished, in the present embodiment, by governing the state of one control signal to switch circuit 30 over signal line 52 in a high state, and another control signal to switch 30 over signal line 52 in a low state as shown by the time graphs of FIGS. 4B and 4A, respectively. During this period from $t_0$ to $t_1$, the voltage across the thermistor bead 22, which is monitored by amplifier/buffer 32, is passed to inputs B and A of the differential amplifier 36 directly from amplifier 32 and through the sample-and-hold circuit 38 as shown by the time graphs of FIGS. 4E and 4D, respectively. The time period $t_0$–$t_1$ is made long enough to permit the voltage across the bead 22 to stabilize substantially in response to the low current level being conducted therethrough.

At or around time $t_1$, controller 50 is operative to control the constant current circuit 20 to conduct current at the second or high current level through the thermistor bead 22 for a period of time, like until time $t_3$, for example. This is accomplished, in the present embodiment, by governing the state of the other control signal to switch circuit 30 over signal line 52 in a high state, and the one control signal to switch 30 over signal line 52 in a low state as shown by the time graphs of FIGS. 4A and 4B, respectively. Also, at or around time $t_1$, the controller 50 is operative to control sample-and-hold circuit 38 via signal line 54 as shown in FIG. 4C to capture the bead voltage and hold it for the duration from $t_1$ to $t_3$, for example, as shown in the time graph of FIG. 4D. Thus, the voltage signal at input A of the differential amplifier 36 remains substantially constant at the stabilized voltage of bead 22 in response to the low current level.

During this period from $t_1$ to around $t_3$, the voltage across the thermistor bead 22 is passed to input B of the differential amplifier 36 directly from amplifier 32, but not passed through the sample-and-hold circuit 38 as shown by the time graphs of FIGS. 4E and 4D, respectively. The time period $t_1$ to $t_3$ is made long enough to permit the voltage across the bead 22 to stabilize substantially in response to the high current level being conducted therethrough as shown by the graph of FIG. 4E. Also, during the period from $t_1$ to $t_3$, the differential amplifier circuit 36 generates a signal indicative of the difference in voltage across the thermistor bead 22 in response to the low and high current levels, or essentially the slope of the voltage characteristic curve of the thermistor bead 22, which is shown by the solid line in the time graph of FIG. 4F.

Comparator 40 compares the bead voltage difference or slope signal from amplifier 36 to a reference signal (see dashed line in FIG. 4F) and generates a signal indicative of the comparison results as exemplified in the time graph of FIG. 4G. The reference signal may be set between the slopes of the thermistor characteristic curves indicative of a wet state and the thermistor characteristic curves indicative of a dry state for all operating temperatures (see FIG. 1). Thus, when the slope signal from amplifier 36 exceeds the reference voltage, comparator circuit 40 may generate an output signal in a high state indicative of a wet bead state as shown by the time graph of FIG. 4G at time $t_2$, for example. Of course, if the slope signal from amplifier 36 does not exceed the reference voltage during the time $t_1$ to $t_3$, the output signal of comparator circuit 40 may remain in a low state indicative of a dry bead state.

In the present embodiment, the controller 50 waits until the voltage across the bead 22 is substantially stabilized in response to the high current level before it controls the latch circuit 44 via signal line 56 to capture the comparison results of comparator 40. Accordingly, at or around time $t_3$, controller 50 issues a pulse over signal line 56 to latch 44 (see time graph of FIG. 4H) to control the capture of the comparison result. Thus, after time $t_3$, the output of latch circuit 44 is indicative of the dry/vet state of the thermistor bead 22. The controller 50 may comprise circuits of many different configurations to issue the control signals over lines 52, 54 and 56 in a time sequence as exemplified by the time graphs of 4A–4C and 4H. For example, the controller 50 may be comprised of a counter which is driven to count through a predetermined count by a clock signal and decoders for issuing the control signals at predetermined counts. Controller 50 may also be embodied with a programmed read only memory which outputs the four control signals shown in FIGS. 4A–4C and 4H as governed by the counter which may be coupled to the address inputs thereof. The clock frequency and length of the counter will be determined by the response times of the thermistor bead to the low and high current levels. In any event, the controller 50 may be configured to repeat the time sequence of time graphs 4A–4I for detecting the dry/wet states of the thermistor bead periodically or at predetermined time intervals.

While the present embodiment utilizes a controller for controlling the time sequencing of operations of the various circuits of the detection circuitry, it is understood that such circuits may alternatively operate autonomously without the need of a central control unit. For example, the constant current source 20 may be operative to alternately select the low current level and high current level for conduction through the thermistor bead for predetermined stabilization time periods. In addition, the sample-and-hold circuit 38 may determine when the voltage across the bead 22 has stabilized, and capture and hold the voltage at the output thereof until the next voltage has stabilized, for example. Still further, the latch circuit 44 may monitor the voltage difference signal output from circuit 36 and not capture the comparison result until after the voltage difference signal has stabilized, for example.

In addition, while the present embodiment sequences the low current level and then the high current level through the thermistor bead for determining the slope of the I/V characteristics thereof as a measure of its dry/wet state, it is understood that the sequence could be reversed and the downstream detection circuitry modified to accommodate the change in polarity of the voltage difference or slope signal as a result of the reversal. Such a modification is also considered clearly within the broad principles of the present invention.

Accordingly, while the present invention has been described herein above in connection with one or more possible embodiments, it is understood that there is no intention to limit the invention in any way, shape or form by such embodiments. Rather, the present invention should be construed in breadth and broad scope in accordance with the recitation of the claims appended hereto.

What is claimed is:

1. Method of detecting a dry/wet state of a thermistor bead comprising the steps of:
conducting current through said thermistor bead selectively between first and second predetermined current levels;
measuring a difference in voltage across said thermistor bead in response to said first and second predetermined current levels; and
detecting said dry/wet state of said thermistor bead based on said measured difference in voltage.

2. The method of claim 1 wherein the first and second current levels conducted through the thermistor bead are both less than forty-five milliamps.

3. The method of claim 1 wherein the first and second current levels conducted through the thermistor bead are both less than thirty milliamps.

4. The method of claim 1 wherein the first current level conducted through the thermistor bead is on the order of fifteen milliamps and the second current level conducted through the thermistor bead is on the order of twenty-five milliamps.

5. The method of claim 1 wherein the step of conducting current includes the steps of:
selecting current at the first level to be conducted through the thermistor bead for a period of time to permit the voltage across the thermistor bead in response thereto to stabilize substantially; and
then, selecting current at the second level to be conducted through the thermistor bead for a period of time to permit the voltage across the thermistor bead in response thereto to stabilize substantially.

6. The method of claim 5 wherein the step of measuring includes the steps of:
capturing the substantially stabilized voltage value across the thermistor bead in response to the first current level; and
determining the difference between the captured voltage value and the substantially stabilized voltage value across the thermistor bead in response to the second current level.

7. The method of claim 6 wherein the step of detecting includes the steps of:
comparing the determined voltage value difference with a reference voltage value;
capturing the comparison result at a time after the voltage across the thermistor bead in response to the second current level has stabilized substantially; and
using the captured comparison result to detect the dry/wet state of the thermistor bead.

8. The method of claim 1 wherein the step of detecting includes the steps of:
comparing the measured voltage difference with a reference voltage value; and
using the results of said comparison to detect the dry/wet state of the thermistor bead.

9. The method of claim 1 wherein the steps of conducting, measuring and detecting are repeated at predetermined time intervals to detect the dry/wet state of the thermistor bead at each said time interval.

10. The method of claim 1 wherein the steps of conducting, measuring and detecting are repeated periodically to detect the dry/wet states of the thermistor bead in time.

11. Apparatus for detecting a dry/wet state of a thermistor bead comprising:
a first circuit coupled to said thermistor bead for conducting current through said thermistor bead selectively between first and second predetermined current levels;
a second circuit coupled to said thermistor bead for measuring a difference in voltage across said thermistor bead in response to said first and second predetermined current levels; and
a third circuit coupled to said second circuit for detecting said dry/wet state of said thermistor bead based on said measured difference in voltage.

12. The apparatus of claim 11 wherein the first circuit includes a constant current source coupled to the thermistor bead and operative to conduct current at the first level through the thermistor bead for a period of time to permit the voltage across the thermistor bead in response thereto to stabilize substantially, and then, to conduct current at the second level through the thermistor bead for a period of time to permit the voltage across the thermistor bead in response thereto to stabilize substantially.

13. The apparatus of claim 12 wherein the constant current source includes: a first constant current source for generating current at the first level; a second constant current source for generating current at the second level; and a switch for coupling selectively the first and second constant current sources to the thermistor bead for conducting the selected current through the thermistor bead for the stabilizing period of time.

14. The apparatus of claim 12 wherein the second circuit includes: a circuit coupled to the thermistor bead for capturing the substantially stabilized voltage value across the thermistor bead in response to the first current level; and a circuit coupled to the capturing circuit and the thermistor bead for determining the difference between the captured voltage value and the substantially stabilized voltage value across the thermistor bead in response to the second current level.

15. The apparatus of claim 14 wherein the capturing circuit comprises a sample-and-hold circuit; and wherein the voltage difference determining circuit comprises a differential amplifier.

16. The apparatus of claim 14 wherein the third circuit includes: a comparator circuit coupled to the voltage difference determining circuit for comparing the determined voltage value difference with a reference voltage value; and a latch circuit coupled to the comparator circuit for capturing an output signal of the comparator circuit at a time after the voltage across the thermistor bead in response to the second current level has stabilized substantially, said captured output signal being indicative of the dry/wet state of the thermistor bead.

17. Apparatus for detecting a dry/wet state of a thermistor bead comprising:

a first circuit coupled to said thermistor bead for conducting current through said thermistor bead selectively between first and second predetermined current levels;

a second circuit coupled to said thermistor bead for measuring a difference in voltage across said thermistor bead in response to said first and second predetermined current levels;

a third circuit coupled to said second circuit for detecting said dry/wet state of said thermistor bead based on said measured difference in voltage; and a controller coupled to the first, second and third circuits for controlling the operations thereof in a predetermined time sequence.

18. The apparatus of claim 17 wherein the controller is operative to control the first circuit to conduct current at the first level through the thermistor bead for a period of time to permit the voltage across the thermistor bead in response thereto to stabilize substantially, and then, to conduct current at the second level through the thermistor bead for a period of time to permit the voltage across the thermistor bead in response thereto to stabilize substantially.

19. The apparatus of claim 18 wherein the controller is operative to control the second circuit to capture the substantially stabilized voltage value across the thermistor bead in response to the first current level; and wherein the second circuit is operative to determine the difference between the captured voltage value and the substantially stabilized voltage value across the thermistor bead in response to the second current level.

20. The apparatus of claim 19 wherein the third circuit is operative to compare the voltage value difference determined by the second circuit with a reference voltage value; and wherein the controller is operative to control the third circuit to capture the comparison result at a time after the voltage across the thermistor bead in response to the second current level has stabilized substantially, said captured result being indicative of the dry/wet state of the thermistor bead.

* * * * *